United States Patent [19]

Cecere et al.

[11] 4,065,353

[45] Dec. 27, 1977

[54] METHOD FOR THE PREPARATION OF D-CARBAMYL AMINOACIDS AND THE CORRESPONDING D-AMINOACIDS

[75] Inventors: Francesco Cecere; Giuliano Galli; Gino Della Penna, all of Monterotondo; Bruno Rappuoli, Rome, all of Italy

[73] Assignee: Snamprogetti, S.p.A., Milan, Italy

[21] Appl. No.: 685,318

[22] Filed: May 11, 1976

[51] Int. Cl.$^2$ ............................................ C12D 13/06
[52] U.S. Cl. ............................................ 195/2; 195/29
[58] Field of Search ........................................ 195/2, 29

[56] References Cited

U.S. PATENT DOCUMENTS 3,964,970  6/1976  Dinelli et al. ............... 195/29 X Primary Examiner—R. B. Penland
Attorney, Agent, or Firm—Morgan, Finnegan, Pine, Foley & Lee

[57] ABSTRACT

An enzymatic hydrolysis method is disclosed for the preparation of D-carbamyl aminoacids and the corresponding D-aminoacids.

The method is based on the use of certain substituted hydantoins as the starting materials and these are hydrolized, in a temperature range from 10° C to 70° C, with hydropyrimidine hydrolase from calf livers. The pH range is from 8 to 9.

The method in question is cheaper and more reliable than those of the prior art.

4 Claims, No Drawings

METHOD FOR THE PREPARATION OF D-CARBAMYL AMINOACIDS AND THE CORRESPONDING D-AMINOACIDS

This invention relates to the separation by the enzymatic way of the optical antipodes or enantiomers of aminoacids to obtain the aminoacid having the D-configuration.

A few aminoacids having the D-configuration (such as phenylglycine, p-hydroxyphenylglycine) have taken in recent times a considerable importance as intermediates for the preparation of compounds widely used in the industry.

The chemical methods as used heretofore for the separation of the optical antipodes or enantiomers are based on the use of camphosulfonic acid.

The latter product is extremely expensive, it can be recovered with a low yield only and is not readily available so that the cost of the chemical process is very high.

Another method comprises the steps of acylating the racemic aminoacid, selectively hydrolyzing with the acylase enzyme the D-form and isolating same. However, the D-acylases are comparatively rare and always impure for L-acylase so that during the hydrolysis process of the acylated derivative there are not negligible quantities of the L-antipode or L-enantiomer and this is conducive to obtaining a product having poor optical purity.

There is known from the U.S. Pat. application Ser. No. 469,019 filed on May 10, 1974, now U.S. Pat. No. 3,964,970, in the name of the assignee of this application, a method for the preparation of 1-carbamyl aminoacids and the corresponding aminoacids by the enzymic route starting from substituted hydantoins, the latter being subjected to an enzymic hydrolysis within a pH range from 6 to 11. The reaction is developed towards the formation of the final laevorotatory compounds with a possible recycling of the nonhydrolyzed form.

We have now found, that if the hydantoin concerned is substituted by radicals which contain at least an aromatic group bonded to the asymmetrical carbon atom and the reaction is carried out within a narrower pH range, the reaction proceeds both selectively and quantitatively until the D-form, alone, is obtained.

It has been surprisingly ascertained, in fact, that the enzyme extracted from calf liver and classified as hydropyrimidine hydrolase (E.C. 3.5.2.2.) acts upon the racemic form of compounds having the following formula:

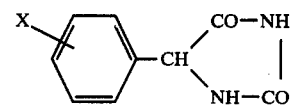

wherein X is —OH, a hydrocarbon radical, a halogen, an alkoxy, —NO$_2$, a carboxyl, by carrying out a rigorous selective hydrolysis of the D-form. The method substantially comprises the step of subjecting to enzymatic hydrolysis compounds having the formula indicated above, which are known as hydantoins substituted in the 5-position. The hydrolysis should be carried out under conditions of pH variable between 8 and 9, preferably 8.5. The temperature can be maintained between 10° C and 70° C, preferably 30° C. The hydrolysis takes place according to the following reaction scheme:

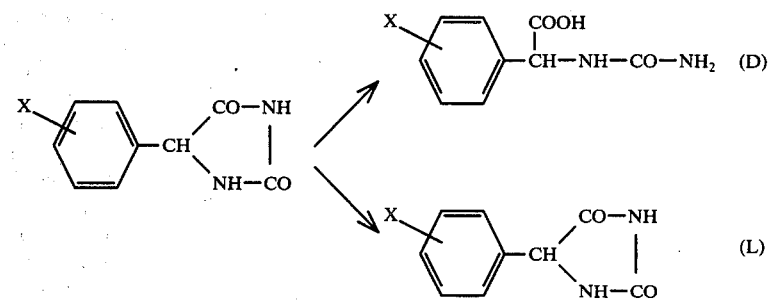

Inasmuch as the D-carbamyl derivative which is formed in the hydrolysis has an acidic nature, it is required that the pH is maintained at the initial value by addition of alkalies as gradually as the reaction proceeds. It has been seen that at the pH values recalled above, while the hydrolysis reaction proceeds, a simultaneous racemization of the remaining L-hydantoin takes place according to the pattern:

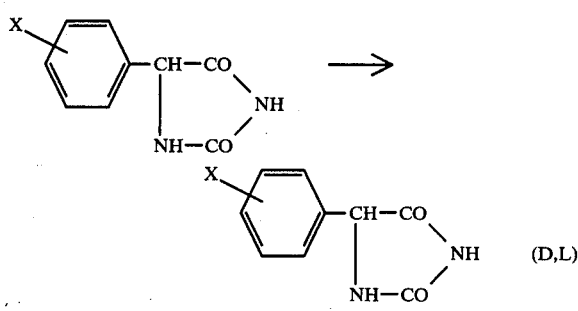

For this reason, as a result of the continuous removal by enzymatic hydrolysis of the D-hydantoin, the final outcome of the reaction is to have all carbamyl derivative of the D-form available. The racemization rate of L-hydantoin is a function both of the temperature and the pH and increased as the temperature pH are increased. However, by operating at a pH in the vicinity of 8.5 the rate is so high that it does not constitute a rate determining step of the reaction.

It has also been found that when the D-carbamyl derivative is dissolved in water and heated to the boiling point under particular conditions it is decomposed according to the following pattern:

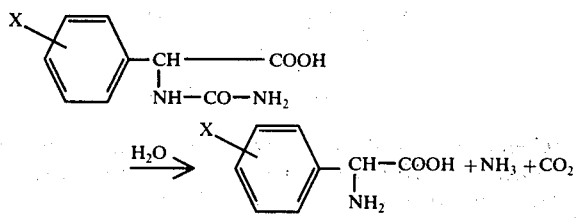

thus forming the optically active aminoacid which can easily be isolated in a form having a very high chemical and optical purity. Lastly, an additional technical and economical improvement to the present invention can be achieved by occluding the enzyme in fibrous structures such as disclosed in the Italian Pat. No. 836,462. By this method, the enzyme, rather than being employed once only, can be repeatedly used, the cost of the operation being thus reduced. In addition, the purification of the reaction product is the simplified, since no proteins having enzymatic activity are left in the reaction mixture.

The following examples are intended better to illustrate the invention but by no way are limitations thereto.

EXAMPLE 1

176 grams (1 mole) of D,L-5-phenylhydantoin are slurried in 7.5 liters of a 0.1M potassium phosphate buffer solution at a pH of 8.5, at 30° C.

The stirred suspension is supplemented by 125 mls of a solution of hydropyrimidine hydrolase from lever. (Total activity 1875 micromols per minute at 30° C, pH 8.5; total proteins 2.75 grams).

After about 6 hours, when, in order to maintain the system at a constant pH there were added 250 mls of 4M NaOH, the reaction has been discontinued and the reaction mixture has been cooled to 4° C and the pH adjusted to 5.5 by addition of 6N—HCl.

During this operation, a mucilaginous precipitate of denaturated proteins has been obtained, which has been removed by centrifuging.

The supernatant, cooled to 4° C again, has been brought to a pH of 2.5 with 6N—HCl. During this operation, a crystalline product precipitates, which is washed with about one liter of cold water and dried to constant weight. The product is crystallized from ethanol-water 70/30 (V/V) in hot conditions.

The crystal (189. grams, yield 97%) is chromatographically homogeneous and on the basis of the IR and NMR and mass spectra and the elemental analysis it has been found to be D(-)-N-carbamyphenylglycine.

The specific optical rotatory power is $[\alpha]_D^{25} = 137°$ C. (C = 1% in $NH_4OH$, 1N) corresponding to the one reported by the literature: T. Suzuki, K. Igarashi, K. Hase, Agr. Biol. Chem. 37(2) 411-416(1973) for D (−)N-carbamyl-phenylglycine.

EXAMPLE 2

A reactor, equipped with a thermostatic jacket having an inlet for nitrogen, an electrode for the pH readings and an inlet for the addition of soda, has been charged with 10 liters of 0.1M phosphate buffer solution which contained hydropyrimidine hydrolase from liver (Total activity: 7500 micromols per minute; total proteins: 11 grams). After having bubbled nitrogen during about 30 mins., the solution, maintained at 30° C, has been supplemented by 192 grams (1 mol) of D,L-5-p.hydroxyphenyl hydantoin while the pH was kept constant by continuous addition of 4M NaOH. After 20 hours, when the consumption of soda has been 250 mls., isolation of D(−)-N-carbamyl-p.hydroxyphenylglycine has been carried out in a manner similar to what has been disclosed in example 1.

The as-obtained raw product has been crystallized from ethanol normal hexane. There have been obtained in this way 152 grams (yield 72%) of a product having the following properties:

melting point: 170° C; $[\alpha]_D^{20} = -170°$ (C=0.5% in water/alcohol 50/50 V/V ).

The structure of the product has been confirmed by the results of the elemental analysis, IR, NMR and mass spectra compared with the data of the literature J. Eagles; W. M. Laird, E. C. Matais, Biochemical Journal, 121, 425-430 (1971) Sup. Publ. No. SUP 50003, Annex 1, Annex 2.

EXAMPLE 3

206 grams (1 mol) of D,L-5-p.methoxyphenyl hydantoin are slurried in 10 liters of 0.1M potassium phosphate buffer at a pH of 8.5 at 30° C, containing hydropyrimidine hydrolase from liver. (Total activity 7500 micromols per minute; total proteins 11 grams).

The pH is maintained constant by continuous addition of 4M NaOH.

After 20 hours, when a consumption of soda of 250 mls was experienced, the reaction has been discontinued and the D(-)-N-carbamyl-p.methoxyphenylglycine has been recovered as disclosed in example 1 with a yield of 90%. The structure of the product has been confirmed by the elemental analysis and the IR, NMR and mass spectra.

EXAMPLE 4

230 mls of a solution of hydropyrimidine hydrolase from liver, having an activity of 10800 micromols per minute and 3.45 grams of proteins, have been added to 2.1 kilograms of a solution of 150 grams of cellulose triacetate in methylene chloride, maintained under a vigorous stirring. The thusly obtained emulsion has been spun according to the method as disclosed in the Italian Patent Specification No. 836.462.

The fiber thus obtained (300 grams) has been introduced in the form of a single hank in a jacketed glass column (dia. 8 centimeters, height 60 centimeters) by securing it at both ends to two stainless steel stirrups. The fiber has been subjected to washings by recycling 4 liters of 0.1M potassium phosphate buffer, pH 8.5, until the enzymatic activity in solution had disappeared (4 washings, 6 hours in total).

The column in which the fiber was contained has then been inserted in a circuit comprising a peristaltic pump for recycling the reaction mixture, a jacketed beaker having an electrode for the continuous check of the pH and an inlet for adding 4M NaOH, actuated by a pH-stat. In the system there have been introduced 5 liters of 0.02 M potassium phosphate buffer at a pH of 8.5 and 176 grams (1 mol) of D,L-5-phenyl hydantoin while the pump was energized for recycling the reaction mixture and the pH-stat actuated for the continuous addition of soda. After 6 hours, as the consumption of 4M NaOH was 250 mls, the reaction has been discontinued. The reaction mixture has been discharged. The fiber has been washed with 4 liters of water. The reactionmixture and the washing waters of the fiber have been concentrated in a vacuo down to about 3 liters, cooled to 2° C and treated with 6N HCl to a pH of 2.5. After a 30-minute digestion, the precipitate has been collected on a filter and dried to constant weight.

The as-obtained product, 180 grams (93% yield) has been found to be D-(−)-N-carbamyl-phenylglycine (m.p. 200° C; $[\alpha]_D^{20} = -135°$ (C = 1% in 1N NH$_4$OH).

EXAMPLE 5

The same system as used in example 4 has been used to obtain D(−)-N-carbamyl-p.hydroxy phenylglycine from D,L-5-para-hydroxyphenylhydantoin, with the exception that the jacketed beaker has been closed and a nitrogen inlet has been added. From 192 grams (1 mol) of D,L-5-p.hydroxyphenylhydantoin, after a 60-hours reaction, there have been obtained as described in the previous examples, 160 grams (yield 76%) of D(−)-N-carbamyl-para-hydroxyphenylglycine (m.p. 200° C; $[\alpha]_D^{20} = -175°$ (C = 0.5% in alcohol/water 50/50 V/V).

EXAMPLE 6

By using the same system as described in example 4, from 206 grams (1 mol) of D,L-5-para-methoxyphenylhydantoin there have been obtained 200 grams (89% yield) of D(−)-N-carbamyl-para-methoxyphenylglycine.

EXAMPLE 7

194 grams (1 mol) of D(−)-N-carbamylphenylglycine, as obtained as disclosed in example 4 have been slurried in 5 liters of water. The suspension has been adjusted to a pH of 4 with a saturated solution of Na$_2$CO$_3$.

The suspension is boiled during the 8 hours whereas the pH which tended to rise was occasionally adjusted from 5 to 4 by addition of Amberlite I.R.120 (H$^{30}$). (The total addition has been 400 mls of resin). Then the hot solution has been stripped of the resin, concentrated in a vacuo to 1 liter, cooled and treated with 6N HCl to a pH of 2. The crystal which has been obtained has been collected on a filter, washed with water and dried in a vacuo to a constant weight.

There have thus been obtained 88 grams (0.045 mol) of D(−)-N-carbamylphenylglycine. $[\alpha]_D^{20} = -136.9°$). From the crystallization liquor of this product, adjusted to a pH of 6 and concentrated in a vacuo, there have been obtained 70 grams (0.46 mol) of D(−)-phenylglycine. $[\alpha]_D^{20} = -154°$ (C = 1% in 1N HCl). The structure of the product has been confirmed by elemental analysis and IR, NMR and mass spectra.

EXAMPLE 8

In a manner similar to that disclosed in example 7, but carrying out the reaction in a nitrogen atmosphere, from 210 grams (1 mol) of D(−)-N-carbamyl-para-hydroxy-phenylglycine, after 9-hour boiling there have been obtained 67 grams (40% yield) of D(−)-para-hydroxyphenylglycine $[\alpha]_D^{20} = -154°$ (C = 0.5% in 1N HCl).

The nonhydrolyzed D(−)-N-carbamyl-para-hydroxyphenylglycine was found to be 100 grams (47% yield) and with $[\alpha]_D^{20} = -175°$ C (C = 0.5% in ethanol/water 50/50 V/V).

EXAMPLE 9

As disclosed in example 7, from 224 grams (1 mol) of D(−)-N-carbamyl-para-methoxyphenylglycine as obtained as disclosed in example 3, there have been obtained 80 grams (yield 44%) of D(−)-p.methoxyphenylglycine.

What we claim is:

1. A method for the preparation of D-carbamyl aminoacids comprising the steps of subjecting to enzymatic hydrolysis in the presence of a hydropyrimidine hydrolase and a racemic mixture of compounds having the formula:

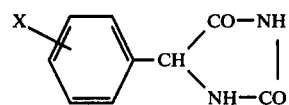

wherein X represents —OH, hydrocarbon radicals, halogen, alkoxyl, —NO$_2$, carboxyls, at a pH between 8 and 9.

2. A method according to claim 1 characterized in that the enzymatic hydrolysis is carried out at a temperature ranging from 10° C to 70° C.

3. A method according to claim 1, characterized in that the enzyme is hydropyrimidine hydrolase from calf liver.

4. A method for the preparation of D-aminoacids which comprises the steps of subjecting to enzymatic hydrolysis in the presence of hydropyrimidine hydrolase from calf liver, a racemic mixture of compounds having the formula:

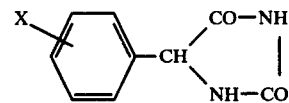

wherein X represents —OH, hydrocarbon radicals, halogen, alkoxyl —NO$_2$ carboxyls, at a pH between 8 and 9 to form D-carbamyl aminoacids and thereafter hydroyzing said D-carbamyl aminoacid to the D-aminoacid by the steps of dissolving said D-carbamyl aminoacid in water to form an aqueous solution and heating said solution to the boiling point to form said D-aminoacid.

* * * * *

UNITED STATES PATENT AND TRADEMARK OFFICE
CERTIFICATE OF CORRECTION

PATENT NO. : 4,065,353

DATED : December 27, 1977

INVENTOR(S) : Francesco Cecere, Giuliano Galli and Gino Della Penna

It is certified that error appears in the above-identified patent and that said Letters Patent are hereby corrected as shown below:

On the cover page after line [22] insert

--Foreign Application Priority Data

May 12, 1975   Italy............23202

Signed and Sealed this

Twentieth Day of February 1979

[SEAL]

Attest:

RUTH C. MASON
*Attesting Officer*

DONALD W. BANNER
*Commissioner of Patents and Trademarks*